US006645975B1

(12) United States Patent
Sit et al.

(10) Patent No.: US 6,645,975 B1
(45) Date of Patent: Nov. 11, 2003

(54) PROCESS FOR THE PREPARATION OF DINAPOSOLINE

(75) Inventors: Sing-Yuen Sit, Meriden, CT (US); Swanee E. Jacutin-Porte, Woburn, MA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/343,037

(22) PCT Filed: Aug. 10, 2001

(86) PCT No.: PCT/US01/25265

§ 371 (c)(1), (2), (4) Date: Jan. 27, 2003

(87) PCT Pub. No.: WO02/13827

PCT Pub. Date: Feb. 21, 2002

Related U.S. Application Data

(60) Provisional application No. 60/224,968, filed on Aug. 11, 2000.

(51) Int. Cl.[7] .................... A61K 31/473; C07D 221/18; C07D 491/056

(52) U.S. Cl. ........................... 514/284; 546/75; 546/48; 514/280

(58) Field of Search ................................ 514/284, 280; 546/75, 48

(56) References Cited

FOREIGN PATENT DOCUMENTS

WO 97/06799 * 2/1997 ................. 514/284

OTHER PUBLICATIONS

Sattelkau, T. et al. : An efficient synthesis of the dopamine D1 agonist dinapsoline by construction and selective reduction of 2'–azadimethoxybenzanthrone. Synthesis, vol. 2, pp. 262–266, 2001.*

* cited by examiner

*Primary Examiner*—Charanjit S. Aulakh
(74) *Attorney, Agent, or Firm*—Barnes & Thornburg

(57) ABSTRACT

The present invention relates to a novel process for the preparation of compounds of the formula

IX

OR2 R4 R1O A R5 R6 N R wherein $R^1$, $R^2$, $R^4$, $R^5$, $R^6$ and A are as defined herein, and to certain derivations of Formula IX which are useful for the treatment of movement disorders.

13 Claims, No Drawings

PROCESS FOR THE PREPARATION OF DINAPOSOLINE

CROSS-REFERENCE TO RELATED APPLICATIONS

This application is a U.S. national counterpart application of international application serial No. PCT/US01/25265 filed Aug. 10, 2001, which claims priority to U.S. provisional application serial No. 60/224,968 filed Aug. 11, 2000.

FIELD OF THE INVENTION

The present invention provides a process for the preparation of dinapsoline and certain derivatives thereof which are useful as dopamine receptor agonists in the treatment of movement disorders.

BACKGROUND OF THE INVENTION

Dopamine has been implicated in numerous neurological disorders. It is generally recognized that either excessive or insufficient functional dopaminergic activity in the central and/or peripheral nervous system may cause hypertension, narcolepsy, and other behavioral, neurological, physiological, and movement disorders including Parkinson's disease, a chronic, progressive disease characterized by an inability to control the voluntary motor system.

A number of ligands for the treatment of dopamine-related dysfunction of the central and peripheral nervous system are described in International Patent No. WO 97/06799, published Feb. 27, 1997, having the general tetrahydro-1H-naph[1,2,3-de]isoquinoline chemical structure described below.

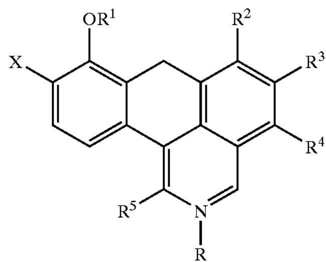

In particular, the international application specifically describes the synthesis and use of (±)-8,9-dihydroxy-2,3,7,11b-tetrahydro-1H-naphtho[1,2,3-de]isoquinoline denominated as "dinapsoline" in the description. The synthesis of dinapsoline is depicted generally in FIGS. 1 and 2 as well as in the experimental section. Further description of the synthesis and pharmacological evaluation of dinapsoline is described by D. Ghosh, et al. in *J. Med. Chem.*, Vol. 39, pp. 549–555 (1996).

Although the prior art process works on a small scale, the overall process is a long synthesis which involves as many as 14 steps to complete, including protection and deprotection schemes. The cyclization step near the end of the synthesis was found to be problematic and the yield not reproducible, if there is any product at all. Thus, there is a need for a simple, convenient, economical and scale-up for the preparation of dinapsoline and derivatives thereof. The present inventors have found a suitable process that avoids the problematic cyclization step which uses an isoquinoline system and a highly regloselective carbon-carbon bond forming technique to establish the entire tetracyclic framework in a few simple steps.

SUMMARY OF THE INVENTION

The present invention relates to fused isoquinoline compounds of the formula

IX

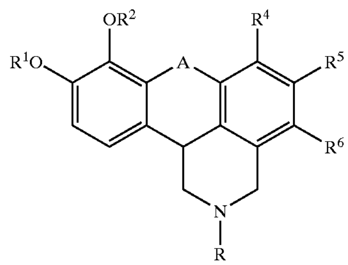

wherein $R^1$, $R^2$, $R^4$, $R^5$, $R^6$ and A are as defined herein which are useful for the treatment of movement disorders. More specifically, the invention relates to a process for their preparation.

DETAILED DESCRIPTION OF THE INVENTION

The present invention relates to a novel process for the preparation of dinapsoline and derivatives thereof which are useful for the treatment of movement disorders, and have the formula

IX

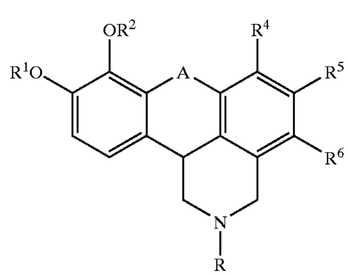

wherein $R^1$ and $R^2$ each are independently hydrogen or a hydroxy-protecting group; or $R^1$ and $R^2$ may be joined together to form —$(CH_2)_n$—; n is 1 to 3; A is $CH_2$, $CHOR^1$ or C═O; and $R^4$, $R^5$ and $R^6$ each are independently hydrogen, $C_{1-4}$alkyl, $C_{1-4}$alkoxy, hydroxy or halogen. The novel and improved process is illustrated in Reaction Scheme 4.

The present invention also provides certain dinapsoline derivatives of Formula IX which are useful for the treatment of movement disorders.

The term "$C_{1-4}$ alkyl" as used herein and in the claims (unless the context indicates otherwise) means straight or branched chain alkyl groups such as methyl, ethyl, propyl, isopropyl, butyl, isobutyl and t-butyl. The term "$C_{1-4}$ alkoxy" as used herein and in the claims means straight or branched chain alkoxy groups such as methoxy, ethoxy, propoxy and butoxy. Preferably, these groups contain from 1 to 2 carbon atoms. Unless otherwise specified, the term "halogen" as used herein and in the claims is intended to include bromine, chlorine, iodine and fluorine while the term "halide" is intended to include bromine, chloride and iodide anion. The term "A" as used herein and in the claims is independently selected from a methylene (—$CH_2$—) group, a hydroxy or hydroxy-protected methylene (—$CHOR^1$) group or a carbonyl (C═O) group.

The term "hydroxy-protecting group" refers to those groups well known to those skilled in the art which can be employed in the present invention to block or protect the hydroxyl group. Preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation.

Suitable hydroxy-protecting groups include acyl groups such as acetyl, propionyl, butyryl, chloroacetyl, dichloroacetyl and trichloroacetyl, phenoxycarbonyl, benzyloxycarbonyl, benzhydryloxycarbonyl, trityloxycarbonyl, p-nitro-benzyloxycarbonyl and 2,2,2-trichloroethoxy-carbonyl; aroyl groups such as benzoyl and substituted benzoyl, for example, methoxybenzoyl, nitrobenzoyl, methylbenzoyl and the like; alkyl groups such as methoxymethyl, benzyloxymethyl, alkyl; aralkyl groups such as benzyl, benzhydryl, trityl or p-nitrobenzyl; or triorganosilyl groups such as tri($C_1$–$C_6$)alkylsilyl (e.g. trimethylsilyl, triethylsilyl, triisopropylsilyl, isopropyidimethylsilyl, t-butyidimethylsilyl, methyldliso-propyisilyl or methyldi-t-butylsilyl), triarylsilyl (e.g. triphenyl-silyl, tri-p-xylsilyl) or triaralkylsilyl (e.g. tribenzysilyl). Examples of these and other suitable hydroxy-protecting groups and methods for their formation and removal are known in the art, e.g. see *Protective Groups in Organic Synthesis*, T. W. Greene, John Wiley & Sons, New York, 1991, Chapter 2, and references therein.

Preferred hydroxy-protecting groups are acyl groups such as acetyl, propionyl and chloroacetyl; aroyl groups such as benzoyl and substituted benzoyl and aryl groups such as benzyl and substituted benzyl. Most preferably, the hydroxy-protecting group is achieved when $R^1$ and $R^2$ are joined together to form a methylene (—$CH_2$—) group.

It should be appreciated by those skilled in the art that the final deblocking step will naturally vary depending on the protecting groups present in substituents $R^1$ and $R^2$. The deblocking step such as illustrated in Reaction Scheme 4, step (g), to produce compounds of Formula IX wherein R1 and $R^2$ are hydrogen is accomplished by conventional procedures such as hydrolysis, chemical reduction, hydrogenation and the like, and includes the method illustrated for the removal of the hydroxy-protecting group wherein $R^1$ and $R^2$ are joined together to form —$CH_2$—.

The compounds of Formula IX may be prepared by various procedures such as those illustrated herein in the examples, in the Reaction Schemes and variations thereof which would be evident to those skilled in the art. The fused isoquinolines of Formula IX may advantageously be prepared by reduction methods from benzo benzoisoquinoline compounds of Formula VII followed by removal of the hydroxy-protecting groups as illustrated in Reaction Scheme 4. The various benzo benzoisoquinolines of Formula VII may advantageously be prepared using free radical carbon-carbon bond formation from aryl isoquinolines of Formula VI as illustrated in Reaction Scheme 3 while the aryl isoquinolines of Formula V may be prepared from isoquinolines of Formula I and appropriately substituted phenyl derivatives by the method illustrated in Reaction Scheme I and the alternative method illustrated in Reaction Scheme 2.

REACTION SCHEME 1

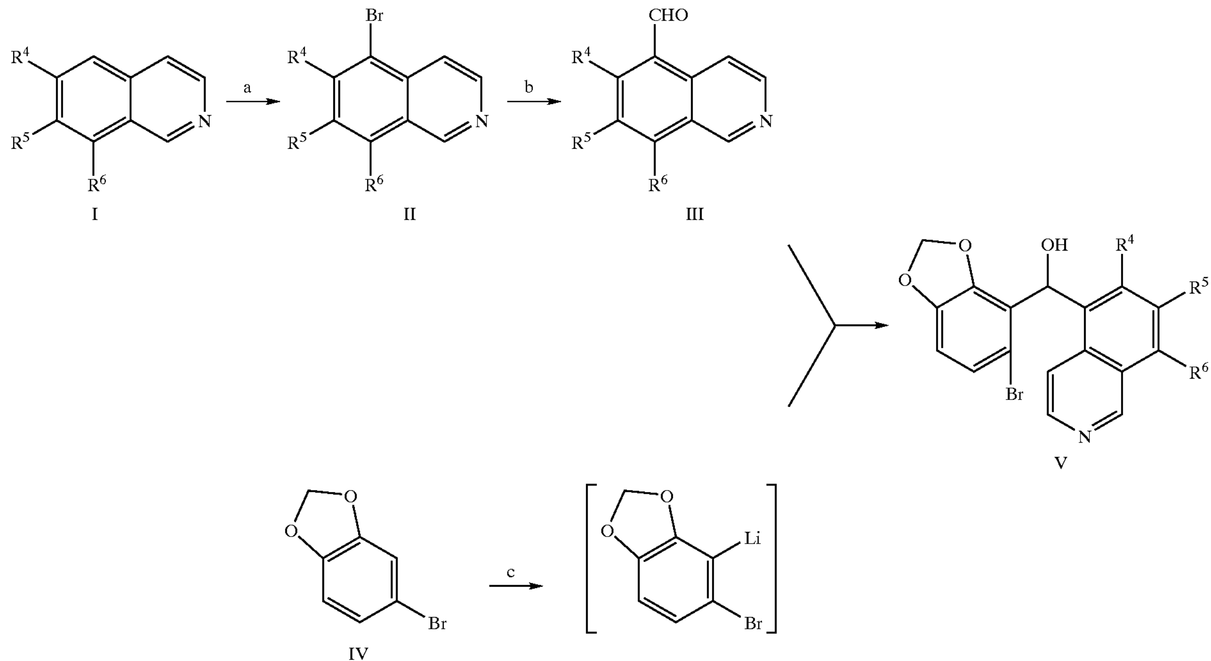

As illustrated in Reaction 1, the compounds of Formula V may be prepared from substituted or unsubstituted isoquinolines of the Formula I which are generally known to undergo electrophilic substitution preferentially at the 5-position to give 5-bromo-isoquinolines of the Formula II. The bromination reaction (a) can be done in neat form and in the presence of a Lewis Acid catalyst such as anhydrous aluminum chloride, or alternatively, the bromination can be carried out in an inert organic solvent such as methylene chloride. In both cases, the overall yields are comparable to each other, and preferably, the bromination is carried out in neat form since it avoids the additional solvent evaporation step. The 5-bromo-isoquinoline compound of Formula II can be trans-metallated to the corresponding 5-lithioisoquinoline using n-butyl lithium in a suitable inert organic solvent such as THF and the reaction is preferably carried out at a temperature below −50 to −80° C. This versatile 5-lithio-isoquinoline can be alkylated, acylated into a variety of 5-substituted isoquinolines. The addition of DMF to said 5-lithio-isoquinoline followed by warming to room temperature and neutralization with an equivalent amount of mineral acid, this 5-lithio-isoquinoline produced the 5-formyl-isoquinoline of Formula III in excellent yields. Using a recently published procedure described by R. Mattson, et al., in *ACS Organic Division*, 1998, Boston Abstract No. 059, the aldehyde of Formula ill may advantageously be reacted with the 4-bromo-3-lithio-1,2-(methylenedioxy)benzene derived from the corresponding hydrocarbon precursor of Formula IV to furnish the desired benzhydrol of Formula V, in crystalline form.

REACTION SCHEME 2

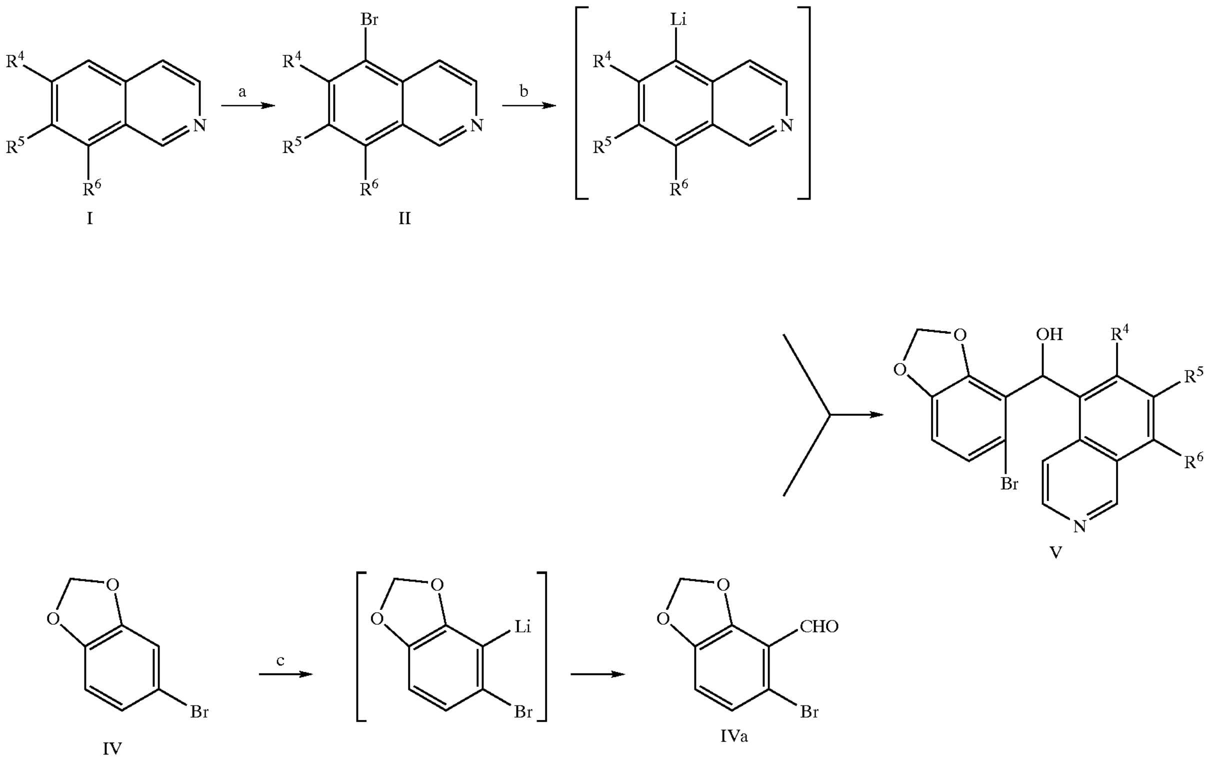

Reagents: (a) $Br_2/AlCl_3$/neat; (b) LDA then IVa; (c) n-BuLi then DMF

The desired compounds of Formula V can alternatively be prepared by a similar but different route which differs in the formulation step as illustrated in Reaction Scheme 2.

The formulation reaction in converting the compound of Formula II to the compound of Formula III which is described above and shown in Reaction Scheme I can be carried out on 4-bromo-3-ithio-1,2-(methylenedioxy) benzene to give the corresponding 2-bromo-5,6-(methylenedioxy)benzaldehyde, of Formula IVa. The aldehyde of Formula IVa is then readily reacted with the lithiated 5-bromo-isoquinoline to produce the identical benzhydrol of Formula V. These complementary and convergent processes are provided to accommodate different pairs of isoquinolines and 4-bromo-1,2-(methylenedioxy)benzenes of the present invention.

REACTION SCHEME 3

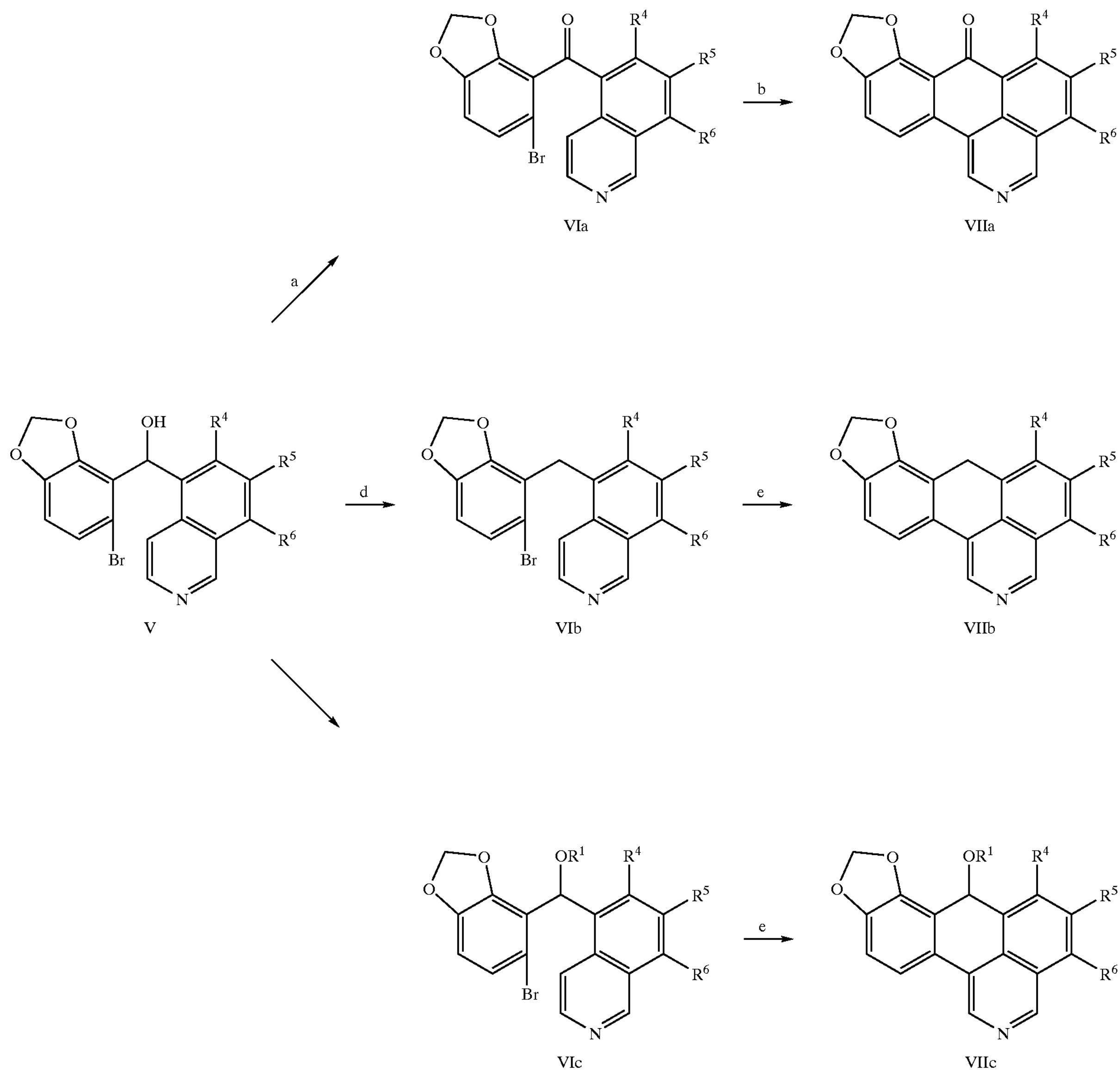

Reagents: (a) $MnO_2$/benzene; (b) n-$Bu_3SnH$/AIBN; (d) $Et_3SiH$/TFA; (e) n-$Bu_3SnH$/AIBN The benzhydrols of Formula V can readily be converted to the aryl isoquinolines of Formulas VIa; VIb and VIc which are useful intermediates for the preparation of dinapsoline and derivatives thereof. It should be appreciated by those skilled in the art that the alcohol of Formula V can readily be oxidized to the corresponding ketone of Formula VIa in a conventional manner with an oxidizing agent such as magapese dioxide. The alcohol of Formula V can readily be protected with a hydroxy-protecting group to afford the compound of Formula Vic while reduction provides the compound of Formula VIb.

The cyclization of the compound of Formulas VIa, VIb and VIc to the corresponding compounds of Formulas VIa, VIIb and VIIc can be initiated by a variety of reaction conditions well-known to those skilled in the art. However, it was found that the best results were achieved by free radical initiated carbon-carbon bond formation since this method was the least sensitive to the electronic environment of the selected precursor. The carbon-carbon bond reaction is preferably carried out with a hydrogen radical source such as trialkyltin hydride, triaryltin hydride, trialkylsilane, triarylsilane or the like and a radical initiator such as 2,2'-azobisisobutylronitrile, sunlight, controlled potential cathodic (Pt) or the like in the presence of a proton source such as a mineral acid, for example, sulfuric acid and hydrochloric acid or an organic acid, for example, acetic acid, trifluoroacetic acid and p-toluenesulfonic acid. In the conversion of compound of Formula VIb to the cyclized compound of Formula VIIb, it is advantageous and preferred to use tributyltin hydride with a variety of well-known initiators and specifically, 2,2'-azobisisobutylronitrile in the presence of acetic acid.

REACTION SCHEME 4

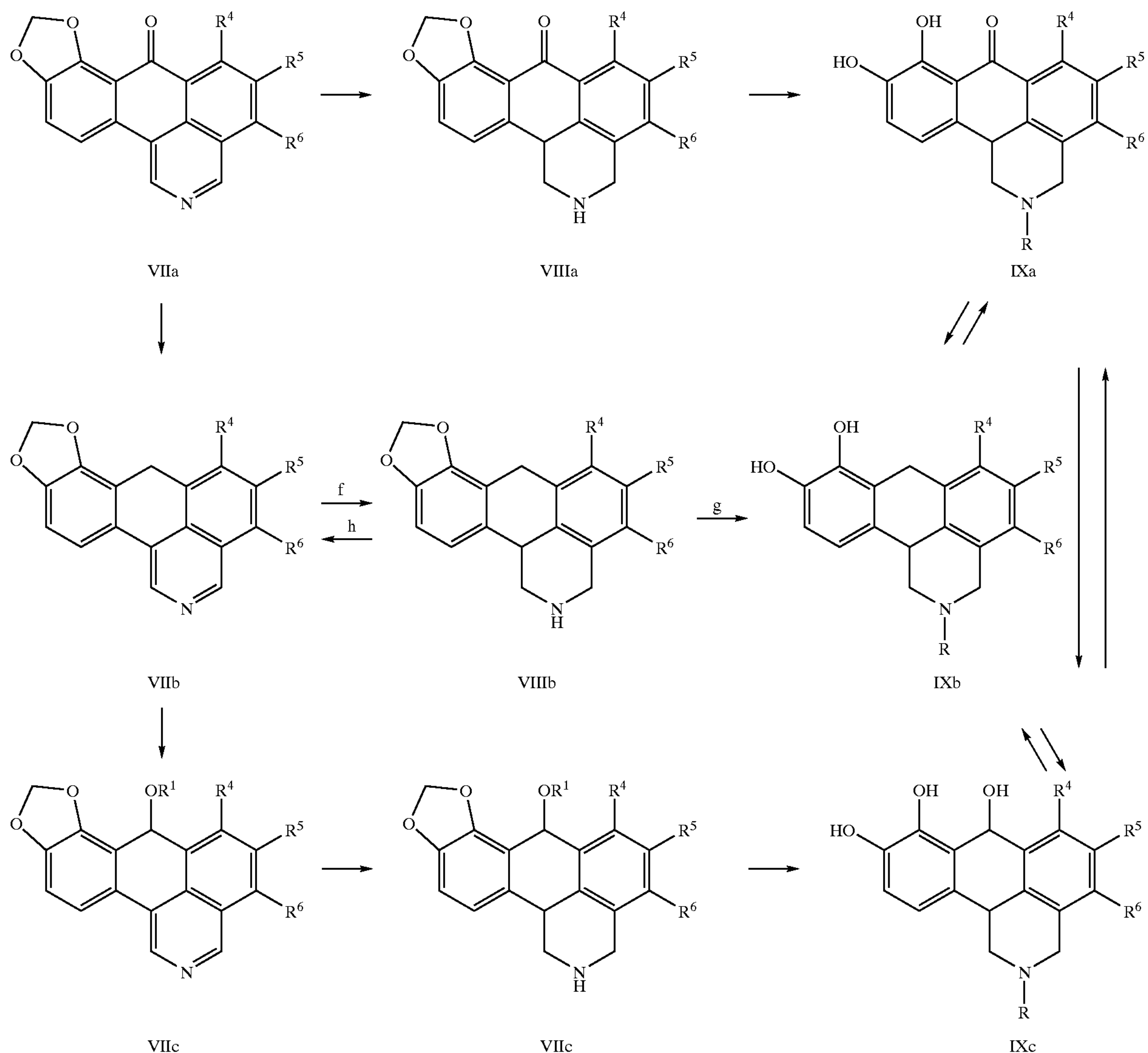

Reagents: (f) $NaBH_3CN$ in HCl/THF; (g) $BBr_3S/CH_2Cl_2$; (h) Pd/C in xylenes

Once cyclized, the intermediates of Formulas VIIa, VIIb and VIIc are useful as starting materials for various, derivatives which differ only at one position in the definition of substituent A as illustrated in Reaction Scheme 4. The compound of Formula VIIb is selectively reduced at the nitrogen bearing heterocyclic ring to give the corresponding tetrahydroisoquinoline of Formula VIIb, the direct precursor of the dinapsoline derivatives of Formula IXb. The selective ring reduction may be carried out by a number of different reduction methods such as sodium cyanoborohydride in an acidic medium in THF, hydride reducing agents such as L-Selectride® or Superhydride® and preferably, catalytic hydrogenation under elevated pressure may be employed. It should be appreciated by those skilled in the art that alternatively, the reverse of said ring reduction can be carried out by using palladium catalyzed dehydrogenation at elevated temperature in an organic solvent such as boiling xylenes. Conversion of the protected compound of Formula VIIIb to the diol of Formula IXb may be accomplished by using boron tribromide in methylene chloride at low temperatures such as −60 to −80° C. and the final product may be isolated in the form of a hydrobromide salt, while the corresponding hydrochloride salt may advantageously be prepared by using boron trichloride instead. If it is desired to prepare the compound of Formula IXb wherein R is $C_{1-4}$ alkyl, then it is advantageous to alkylate the compound of Formula VIIb using conventional methods before the protecting groups are removed to afford the desired diol of Formula IXb.

When it is desired to prepare the corresponding compounds of Formula IX wherein A is a hydroxy group (IXc) or a carbonyl group (IXa) as further illustrated in Reaction Scheme 4, the approximate precursor of Formula VIIIa maybe converted to the desired compound of Formula IXa while the suitably protected compound of Formula VIIIc may advantageously be deprotected to provide the alcohol compounds of Formula IXc. It should be appreciated by those skilled in the art, the conversion of and modification of the A substituent in the compound of Formula IX may be converted readily from one compound to the other by well-known conventional procedures as illustrated in Reaction Scheme 4 for the compounds of Formulas IXa, IXb and IXc.

In a preferred embodiment of the invention the compounds of Formula VI have the formula

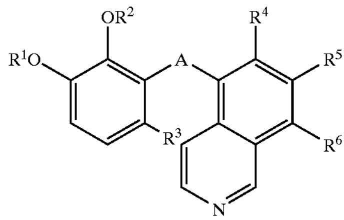

wherein $R^1$ and $R^2$ each are independently hydrogen or a hydroxy-protecting group; or $R^1$ and $R^2$ may be joined together to form —$(CH_2)_n$—; n is 1 to 3, $R^3$ is chloro, bromo or iodo; A is $CH_2$, $CHOR^1$ or C═O; and $R^4$, $R^5$ and $R^6$ each are independently hydrogen, $C_{1-4}$alkyl, $C_{1-4}$alkoxy, hydroxy or halogen. It is most preferred that $R^1$ and $R^2$ are joined together to form —$(CH_2)_n$— wherein n is 1, $R^3$ is bromo, A is $CH_2$ and $R^4$, $R^5$ and $R^8$ are hydrogen.

In another preferred embodiment of the invention the compounds of Formula VII have the formula

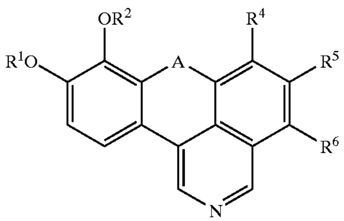

wherein $R^1$ and $R^2$ each are hydrogen or a hydroxy-protecting group; or $R^1$ and $R^2$ may be joined together to form —$(CH_2)_n$—; A is $CH_2$, $CHOR^1$ or C═O; n is 1 to 3; and $R^4$, $R^5$ and $R^6$ each are independently hydrogen, $C_{1-4}$alkyl, $C_{1-4}$alkoxy, hydroxy or halogen. It is most preferred that $R^1$ and $R^2$ are joined together to form —$(CH_2)_n$— wherein n is 1, A is $CH_2$ and $R^4$, $R^5$ and $R^6$ are hydrogen.

In still another preferred embodiment of the invention the compounds of Formula IX have the formula

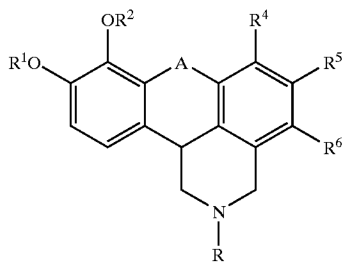

wherein $R^1$ and $R^2$ each are hydrogen or a hydroxy-protecting group; or $R^1$ and $R^2$ may be joined together to form —$(CH_2)_n$—; n is 1 to 3; A is $CHOR^1$ or C═O; R is hydrogen or $C_{1-4}$alkyl; and $R^4$, $R^5$ and $R^6$ each are independently hydrogen, $C_{1-4}$alkyl, $C_{1-4}$alkoxy, hydroxy or halogen. It is most preferred that $R^1$ and $R^2$ are joined together to form —$(CH_2)_n$— wherein n is 1, A is $CH_2$ and R, $R^4$, $R^5$ and $R^6$ are hydrogen.

In another aspect, this invention provides a process for the preparation of a compound of Formula IX

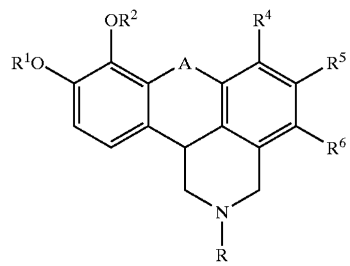

wherein $R^1$ and $R^2$ each are hydrogen; A is $CH_2$, CHOH or C═O; R is hydrogen or $C_{1-4}$alkyl; and $R^4$, $R^5$ and $R^6$ each are independently hydrogen, $C_{1-4}$alkyl, $C_{1-4}$alkoxy, hydroxy or halogen, comprising the steps of (a) reducing a compound of the formula

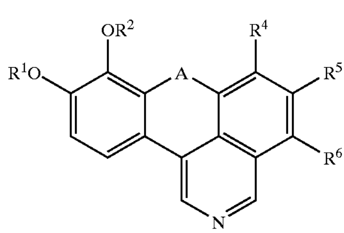

wherein $R^1$ and $R^2$ each are a hydroxy-protecting group; or $R^1$ and $R^2$ may be joined together to form —$(CH_2)_n$— in which n is 1 to 3 and $R^4$, $R^5$ and $R^6$ and A are as defined above; with a reducing agent and (b) deprotectng the resulting reduced product to produce the compound of Formula IX wherein $R^1$ and $R^2$ are hydrogen and (c) optionally, alkylating the product of step (a) or (b) to produce a compound of Formula IX wherein R is $C_{1-4}$alkyl; Preferably, in the process of the invention $R^1$ form —$(CH_2)_n$— wherein n is 1, $R^3$ is bromo, A is $CH_2$ and $R^4$, $R^5$ and $R^6$ are hydrogen and $R^2$ are joined together to form —$(CH_2)$—, A is $CH_2$ and R, $R^4$, $R^5$ and $R^6$ are hydrogen.

Binding to Dopamine Receptors

Dopamine produces biological responses through stimulation of its receptors on cell membranes. The affinity for $D_1$ and $D_2$ receptors were carried out in rat stratum using the in vitro binding assay adapted from C. P. Manik, P. B. Molinoff and P. McGonigle in *J. of Neurochemistry*. Vol. 51, pp. 391–397 (1988) and K. D. Burnis, et al., in *Neuropsychoopharmacology*. Vol. 12, pp. 335–345 (1995). In addition, membranes prepared from HEK-293 cells that express transfected human $D_{2L}$ receptors, sites labeled by the $D_2$ receptor agonist $[^{125}I]$-7-OH-PIPAT were used and the results show that the compounds of the present invention are active in these tests.

In another embodiment, this invention includes pharmaceutical compositions comprising at least one compound of Formula IX in combination with a pharmaceutical adjuvant, carrier or diluent.

In still another embodiment, this invention relates to a method for the treatment of movement disorders a mammal in need thereof, which comprises administering to said mammal a therapeutically effective amount of a compound of Formula IX or a nontoxic pharmaceutically acceptable salt, solvate or hydrate thereof.

In yet another embodiment this invention relates to a method for treating Parkinson's disease in a mammal in need thereof, which comprises administering to said mammal a therapeutically effective amount of a compound of Formula IX or a non-toxic pharmaceutically acceptable salt, solvate or hydrate thereof.

For therapeutic use, the pharmacologically active compounds of Formula IX will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula IX directly in parenteral formulations. The pharmaceutical compositions are prepared by conventional techniques appropriate to the desired preparation containing appropriate amounts of the active ingredient, that is, the compound according to the invention. See, for example, *Remington's Pharmaceutical Sciences*. Mack Publishing Company, Easton, Pa., 17th edition, 1985.

The dosage of the compounds of Formula IX to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula IX or pharmaceutical composition thereof for a mammal, including man, suffering from, or likely to suffer from any condition as described herein is an amount of active ingredient from about 0.1 μg/kg to 100 mg/kg, body weight. For parenteral administration, the dose may be in the range of 1 μg/kg to 10 mg/kg body weight for intravenous administration. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the invention.

DESCRIPTION OF SPECIFIC EMBODIMENTS

All new compounds reported displayed spectral characteristics (IR, MS, $^{1}$H and $^{13}$C NMR) which were consistent with their assigned structures. NMR's were run in the indicated solvent [deuterochloroform ($CDCl_3$) or perdeuterodimethylsulfoxide (DMSO-$d_6$)] at 300 MHz using a Bruker ACP 300 spectrometer. Data are reported as follows: chemical shift (δ) in PPM downfield from calculated tetramethylsilane (TMS); multiplicity (s=singlet, d=cdoublet, t=triplet, q=quartet, p=pentuplet, and br=broadened), integration and coupling constant (given in Hz). Melting points were obtained using a Thomas Hoover capillary apparatus and are uncorrected.

EXAMPLE 1

5-Bromoisoquinoline

The apparatus consisted of a 500 mL three-necked flask equipped with a condenser, dropping funnel and a stirrer terminating in a stiff, crescent-shaped Teflon polytetrafluroethylene paddle. To isoquinoline (57.6 g, 447 mmol) in the flask was added $AlCl_3$ (123 g, 920 mmol). The mixture was heated to 75–85° C. Bromine (48.0 g, 300 mmol) was added using a dropping funnel over a period of 4 hours. The resulting mixture was stirred for one hour at 75° C. The almost black mixture was poured into a vigorously hand-stirred cracked ice. The cold mixture was treated with sodium hydroxide solution (10N) to dissolve all the aluminum salts as sodium aluminate and the oily layer was extracted with ether. After being dried with $Na_2SO_4$ and concentrated, the ether extract was distilled at about 0.3 mm. A white solid (16.3 g, 78 mmol) from a fraction of about 1.25° C. was obtained (26% yield). The product was further purified by recrystallization (pentane or hexanes): mp 80–81° C.;

$^{1}$H NMR (DMSO-$d_6$) δ 9.34 (s, 1H), 8.63 (d, 1H, J=9.0 Hz), 8.17 (d, 1H, J=7.5 Hz), 8.11 (d, 1H, J=6.6 Hz), 7.90 (d, 1K, J=6.0 Hz, 7.60 (t, 1H, J=7.5 Hz); $^{13}$C NMR (DMSO-$d_6$) δ 153.0, 144.7, 134.3, 134.0, 129.3, 128.5, 128.0, 120.3, and 118.6. Anal. Calcd. for $C_9H_6BrN$: C, 51.96; H, 2.91; N, 6.73. Found: C, 51.82; H, 2.91, N, 6.64.

EXAMPLE 2

5-Isoquinolinecarboxaldehyde

To a solution of n-butyllithium (19.3 mL of 2.5M in hexanes, 48 mmol) in a mixture of ether (80 mL) and THF (80 mL) at −78° C. was added dropwise a solution of bromoisoquinoline (5.0 g, 24 mmol) in THF (10 mL). The reaction mixture was stirred at −78° C. under argon for 30 minutes. Following the general procedures described by Pearson, et al., in *J. Heterocycl. Chem.*, Vol. 6 (2), pp. 243–245 (199), a solution of DMF (3.30 g, 45 mmol) in THF (10 mL) was cooled to −78° C. and quickly added to the isoquinolyllithium solution. The mixture was stirred at −78° C. for 15 minute. Ethanol (20 mL) was added followed by saturated $NH_4Cl$ solution. The resulting suspension was warmed to room temperature. The organic layer, combined with the ether extraction layer, was dried over $Na_2SO_4$. A pale yellow solid (2.4 g, 15 mmol, 64% yield) was obtained from chromatography ($SiO_2$ Type-H, 50% EtOAc in hexanes) and recrystallization (ethanol): mp 114–116° C.;

$^{13}$H NMR (DMSO-$d_6$) δ 10.40 (s, 1H), 9.44 (s, 1H), 8.85 (d, 1H, J=6.0 Hz, 8.69 (d, 1H, J=6.0 Hz, 8.45 (m, 2H), 7.90 (t, 1H, J=7.2 Hz); $^{13}$C NMR (DMSO-$d_6$)) δ 194.23, 153.5, 146.2, 140.2, 135.2, 132.6, 130.2, 128.6, 127.5, and 117.2. Anal. Calcd. for $C_{10}H_7NO.0.05H_2O$: C, 75.99; H, 4.53; N, 8.86. Found: C, 75.98; H, 4.66, N, 8.68.

EXAMPLE 3

4-Bromo-1,2-(methylenedioxy)-3-benzaldehyde

To a solution of 4-bromo-1,2-(methylenedioxy)benzene (24.9 mmol) in THF (52 mL) at −78° C., lithium diisopropylamide in 1.5M in cyclohexane (27.4 mmol) was slowly added and the resulting solution was stirred for 15 minutes. DMF (4.15 mL) was then added dropwise and the reaction solution was allowed to warm at room temperature for 1 hour. The solution was washed with saturated $NH_4Cl$ and the organic layer was concentrated and dried under vacuo. The yellow solid product was recrystallized using isopropyl acetate to afford the title compound as yellow needles (69% yield). mp 158–159° C.;

$^1$H NMR ($CDCl_3$) δ 10.29 (s, 1H), 7.08 (d, 1H, J=8.25 Hz, 6.83 (d, 1H J=8.22 Hz), 6.17 (s, 2H); $^{13}$C NMR $CDCl_3$) δ 190.8, 149.8, 149.1, 126.5, 117.7, 115.9, 113.9, 103.8. Anal. Calcd. for $C_8H_5BrO_3$: C, 41.95; H, 2.20; Br, 34.89 Found: C, 41.91; H, 2.09; Br, 34.56.

EXAMPLE 4

α-(5-Bromo-1,3-benzodioxal-4-yl)-5-isoquinolinemethanol

To a solution of 4-bromo-1,2-(methylendioxy)benzene (3.01 g, 15 mmol) in THF (20 mL) at −78° C. was added dropwise lithium diisopropylamide (10.6 mL of 1.5M in cyclohexane, 16 mmol). The reaction mixture was stirred at −78° C. under argon for 20 minutes. A brown solution was formed. A solution of 5-isoquinolinecarboxaldehyde (1.90 g, 12 mmol) in THF (4 mL) was added dropwise. The resulting mixture was stirred at −78° C. for 10 minutes and warmed to room temperature. Stirring was continued for 30 minutes at room temperature, and then the mixture was quenched with saturated NH4Cl solution. The product was extracted with EtOAc and the solvent was removed under reduced pressure. Chromatography (SiO2 Type-H, 35% EtOAc in Hexanes) of the residue yielded the title compound as a yellow solid (2.8 g, 7.8 mmol, 65% yield): mp 173–175° C.;

$^1$H NMR (DMSO-$d_6$) δ 9.32 (s, 1H), 8.47 (d, 1H, J=6.0 Hz), 8.05 (d, 1H, J=8.1 Hz), 7.96 (d, 1H, J=7.2 Hz), 7.76 (d, 1H, J=6.0 Hz), 7.66 (t, 1H, J=7.8 Hz), 7.14 (d, 1H, J=8.1 Hz), 6.84 (d, 1H, J=8.1 Hz), 6.58 (d, 1H, J=8.1 Hz), 6.28 (d, 1H, J=5.4 Hz), 5.95 (s, 1H), 5.80 (s, 1H); $^{13}$C NMR (DMSO-$D_6$) δ 153.1, 147.6, 147.0, 142.9, 136.9, 132.7, 128.9, 128.3, 127.3, 126.7, 125.6, 124.4, 116.3, 114.0, 109.3, 101.6, and 69.0. Anal. Calcd. for $C_{17}H_{12}BrNO_3$: C, 57.01; H, 3.38; N, 3.91. Found: C, 57.04; H, 3.51, N, 3.89.

EXAMPLE 5

α-(5-Bromo-1,3-benzodioxol-4-yl)-5-isoquinolinemethanol

To a solution of 5-bromoisoquinoline (0.50 g, 2.4 mmol) in ether (8 mL) at −78° C. was added dropwise t-butyllithium (3.6 mL of 1.7M in pentane, 6.0 mmol) under argon. The mixture was stirred at −78° C. under argon for 30 minutes then continued for 15 minutes with the flask right above the dry-ice acetone bath. 4-Bromo-1,2-(methylenedioxy)-3-benzaldehyde (0.524 g, 2.4 mmol) was added in one portion at −78° C. under argon. The mixture was stirred at −78° C. for five minutes and then was warmed to room temperature using a water bath. Stirring was continued for 20 minutes at room temperature and then the mixture was quenched with saturated $NH_4Cl$, extracted with EtOAc and dried over $Na_2SO_4$. Chromotography ($SiO_2$, 35% EtOAc in hexanes) yielded the title compound as, a yellow solid (0.18 g, 0.50 mmol, 21% yield) which is identical to the compound of Example 4.

EXAMPLE 6

5-[(5-Bromo-1,3-benzodioxol-4yl)methyl]isoquinoline

To a solution of secondary alcohol α-(5-bromo-1,3-benzodioxol-4-yl)-5-isoquinolinemethanol (8.37 mmol) in trifluoroacetic acid (100 mL), triethylsilane (83.7 mmol) was added and the resulting solution was refluxed for an hour at 70–75° C. and stirred overnight at room temperature. The solvent was removed under vacuo and the residue was dissolved in ethyl acetate washed with saturated $NH_4Cl$ dried over $Na_2SO_4$, filtered and concentrated. Purification was performed by column chromatography to afford the trifluoroacetate salt of the title compound as a white crystalline solid (67% yield): mp 138–140° C.;

$^1$H NMR ($CDCl_3$) δ 9.64 (s, 1H), 8.63 (d, 1H, J=6.59 Hz), 8.45 (d, 1H, J=6.62 Hz), 8.14 (d, 1H, J=8.22 Hz), 7.77 (t, 1H, J=7.39 Hz), 7.64 (d, 1H, J=7.29 Hz, 7.13 (d, 1H, J=8.33 Hz), 6.71 (d, 1H, J=8.31 Hz) 5.94 (s, 2H), 4.53 (s, 2H); $^{13}$C NMR ($CDCl_3$) δ 147.8, 147.7, 147.1, 137.2, 135.1, 134.7, 133.4, 130.3, 128.6, 128.3, 125.9, 120.7, 119.4, 116.3, 109.1, 101.9 and 31.7. Anal. Calcd. for $C_{17}H_{12}BrNO_2.C_2HF_3O_2$: C, 50.02; H, 2.87; Br, 17.51; N, 3.07. Found: C, 49.91; H, 3.02; Br, 17.95; N, 3.04.

EXAMPLE 7

12H-Benzo[d,e][1,31]benzodioxol[4,5-h]isoquinoline

Method A:

A solution of 5-[(5-bromo-1,3-benzodioxol-4-yl)methyl]-isoquinoline (0.357 g, 1.0 mmol) and 2,2'-azobisisobutylronitrile (0.064 g, 0.39 mmol) in benzene (10 mL) was cooled to −78° C., degassed four times with $N_2$ and then heated to 80° C. under argon. A solution of tributyltin hydride (1.14 g, 3.9 mmol) in 10 mL of degassed benzene was added in two hours. TFA (0.185 g, 1.6 mmol) was added in four equal portions (¼ each half hour). The reaction mixture was stirred at 80° C. under argon for six hours after addition of TFA. Additional tributyltin hydride (0.228 g, 0.80 mmol) was added dropwise. The stirring continued overnight (16 hours). Another 2,2'-azobisisobutylronitrile (0.064 g, 0.39 mmol) and TFA (0.093 g, 0.80 mmol) were added in one portion. A solution of tributyltin hydride (1.14 g, 3.9 mmol) in 10 mL of degassed benzene was also added in two hours. More TFA (0.185 g, 1.6 mmol) was added in four equal portions (¼ each half hour). The stirring continued for another six hours and tributyltin hydride (0.456 g, 1.6 mmol) was added dropwise. The reaction mixture was stirred overnight (16 hours). The solvent was removed under reduced pressure. Pentane (100 mL) was added to residue and resulting mixture was cooled to −78° C. A brown gum was formed and filtered. The filtrate was extracted with MeCN. The MeCN layer was combined with the brown gum. The crude product from evaporation of MeCN was purified by chromatography ($SiO_2$ Type-H, 15% EtOAc in hexanes). The isolated compound was dissolved in $CH_2Cl_2$ and extracted with HCl (1N). The aqueous layer was basified to pH~10 using 10N of NaOH solution and reextracted with $CH_2Cl_2$. The organic layer was dried over $Na_2SO_4$. Evaporation of solvent yielded the title compound as an orange solid (0.068 g, 0.26 mmol, 25% yield): mp 194–197° C.;

$^1$H NMR (DMSO-$d_6$) δ 9.12 (s, 1H), 9.06 (s, 1H), 7.93 (d, 1H, J=6.9 Hz), 7.83 (d, 1H, J=8.1 Hz), 7.73 (dd, 1H, J=7.2, 1.5 Hz) 7.66 (t, 1H, J=7.8 Hz), 6.96 (d, 1H, J=8.4 Hz), 6.14 (s, 2H), 4.44 (s, 2H); $^{13}$C NMR (DMSO-$d_6$) δ 150.6, 147.0, 145.2, 135.6, 130.6, 129.3, 129.1, 127.7, 127.5, 125.0, 1.23.6, 117.2, 116.1, 107.5, 101.6, and 26.6. Anal. Calcd. for $C_{17}H_{11}NO_2.0.12CH_2Cl_2$: C, 75.75; H, 4.17; N, 5.16. Found: C, 75.75 H, 4.03, N, 4.83.

Method B:

A solution of 5-[(5-bromo-1,3-benzodioxol-4-yl)methyl]-isoquinoline (12.6 g, 36.8 mmol) and 2,2'-azobisisobutylronitrile (5.92 g, 36.0 mmol) in benzene (1500 mL) was cooled to −78° C., degassed/purged four times with nitrogen and then heated to 80° C. under argon. A solution of tributyltin hydride (39.9 g, 137 mmol) in 30 mL of degassed benzene was added dropwise over a period of three hours. Acetic acid (12.6 g, 210 mmol) was added in one portion before the addition of tin hydride. The reaction mixture was stirred at 80° C. under argon for 16 hours. Excess triethylamine was added to neutralize the residual acetic acid component. The solvent was removed under reduced pressure. Methylene chloride (250 mL) was added to dissolve the semi-solid. It was followed by the addition of hexanes to a point just before the mixture became cloudy. This solution was poured over a short bed of silica gel and the tri-n-butyltin acetate was removed by washing with hexanes until it is no longer, detected by TLC. The product was then eluted out with mixtures of hexanes and ethyl acetate to give the desired title compound (6.1 g, 23.4 mmol, 63.5% yield) which was identical to the product prepared by Method A.

EXAMPLE 8

(±)-8,9-Methylenedioxy-2,3,7,11b-tetrahydro-1H-napth[1,2,3-de]isoguinoline

Method A:

To a solution of 12H-benzo[d,e][1,3]benzodioxol[4,5-h] isoquinoline (6.08 g, 0.33 mmol) in THF (43 mL) was added 2N HCl (1.7 mL, 3.4 mmol) and an orange precipitate formed. Sodium cyanoborohydride (0.274 g, 4.4 mmol) was added in one portion. The resulting suspension was stirred at room temperature for two hours. HCl (2N, 10 mL) was added and stirring continued for 5 minutes. Saturated $NaHCO_3$ solution was added (pH~7–8). The resulting mixture was extracted with EtOAc, dried over $Na_2SO_4$ and the solvent was removed under reduced pressure. Chromatography ($SiO_2$ Type-H, 5% MeOH in $CH_2Cl_2$) of the residue yielded the title compound as a yellow gum (0.066 g, 0.25 mmol, 75% yield);

$^1$H NMR ($CDCl_3$) δ 7.15 (m, 2H), 6.97 (d, 1H, J=6.9 Hz), 6.83 (br, s, 1H), 6.68 (d, 1H, J=8.1 Hz), 6.59 (d, 1H, J=8.1 Hz), 6.01 (d, 1H, J=1.4 Hz), 5.91 (d; 1H, J=1.4 Hz), 4.40–4.00 (m, 5H), 3.55 (dd, H, J=17.7, 3.0 Hz), 3.10 (t, 1H, J=12.0 Hz); $^{13}$C NMR ($CDCl_3$) δ 146.1, 144.8, 136.0, 132.2, 130.4, 128.6, 127.1, 127.0, 124.5, 118.5, 116.2, 106.2, 101.2, 45.8, 35.1, 34.3, and 28.9. Anal. Calcd. for $C_{17}H_{15}NO_2.0.52HCN.1.8H_2O$: C, 67.49; H, 6.18; N, 6.83. Found: C, 67.45 H, 5.96, N, 6.75.

Method B:

12H-Benzo[d,e][1,3]benzodioxol[4,5-h]isoquinoline (11.26 g) was dissolved into 500 mL of glacial acetic acid in a suitable glass liner that will fit into a 1-L Parr "bomb reactor". To this dark amber solution was added 480 mg $PtO_2$ and a magnetic stirring bar. Usual purge cycles were repeated three times at −78° C. Finally hydrogen gas was charged into the steel bomb at 140 PSI while the content was still at −78° C. The reactor was allowed to warm to room temperature over a period of 2 hours while the internal pressure increased to 195 PSI. Gas absorption was faster after about 4 hours at room temperature. After 24 hours, the internal pressure returned to 165 PSI indicating roughly stoichlometric uptake of hydrogen gas. The black suspension was removed after the pressure was relieved, it was filtered over silica gel, rinsed with acetic acid and concentrated under reduced pressure to give about 19 gm of gummy substance. The crude product was neutralized with sodium bicarbonate solution followed by extraction with methylene chloride to yield 11.6 gm of the title compound whose $^1$H NMR was indistinguishable from the purified material prepared above by the Method A.

EXAMPLE 9

5-Bromo-1,3-benzodioxol-4-yl)-(5-isoguinolinyl) methanone

To a solution of secondary alcohol α-(5-bromo-1,3-benzodioxol-4-yl)-5-isoquinolinemethanol (1.39 mmol) in benzene (200 mL), manganese dioxide (28.0 mmol) was added and the reaction mixture was stirred vigorously overnight at room temperature. Excess $MnO_2$ was filtered through Celite, washed with EtOAc (2×) and the filtrate washings were combined and concentrated to give a pure yellow solid, product (quantitative yield). The product was recrystallized with EtOAc/Hexane to afford the title compound: mp 193–195° C.;

$^1$H NMR ($CDCl_3$) δ 9.33 (s, 1H), 8.86 (d, 1H, J=6.09 Hz), 8.71 (d, 1H, J=6.06 Hz), 8.19 (d, 1H, J=8.16 Hz), 7.97 (d, 1H, J=38 Hz), 7.61 (t, 1H, J=8.13 Hz), 7.10 (d, 1H, J=8.28 Hz, 6.81 (d, 1H, J=8.28 Hz), 5.97 (s, 2H); $^{13}$C NMR ($CDCl_3$) δ 192.8, 153.0, 147.7, 146.2, 136.6, 134.3, 133.9, 131.9, 129.1, 126.2, 126.1, 123.4, 118.8, 110.9, 110.7, 102.7. Anal. Calcd. for $C_{17}H_{10}BrNO_3$: C, 57.33; H, 2.83; Br, 22.43; N, 3.93 Found: C, 57.3; H, 2.76; Br, 22.73; N, 3.82.

EXAMPLE 10

12H-Benzo[d,e][1,3benzodioxol4,5-h]isoquinolin-12-one

To a solution of ketone (5-bromo-1,3-benzodioxol-4-yl)-(5-isoquinolinyl)methanone (0.56 mmol) in benzene (12 mL), tributyltin hydride (0.06 mmol) and 2,2'-azobisisobutylronitrile (0.035 mmol) were added and the resulting mixture was refluxed for 40 hours under nitrogen. The solvent was removed in vacuo and the residue was dissolved in acetonitrile and washed with hexane(3×). The extract was concentrated in vacuo and subjected to column chromatography (EtOAc/Hexane). The product was isolated to afford a yellow fluorescent solid. The product was recrystallized (10% yield) with EtOAc/Hexane to afford the title compound: MS (ESI) m/e 275.

$^1$H NMR (DMSO-$d_6$) δ 9.59 (s, 1H), 9.47 (s, 1H), 8.69 (dd, 1H, J=7.50, 1.2 Hz), 8.61 (dd, 1H, J=8.10, 1.20 Hz), 8.26 (d, 1H, J=8.40). 8.02 (t, 1H, J=7.50 Hz, 7.43 (d, 1H, J=8.40 Hz), 6.33 (s, 2H).

EXAMPLE 11

(±)-8,9-Dihydrox-2,3,7,11b-tetrahydro-1H-napth[1,2,3-de]isoquinoline $BBr_3$ (25.0 mL of 1M in $CH_2Cl_2$, 25.0 mmol) was added to a cooled solution (−78° C.) of methylenedioxy dinapsoline as prepared in Example 8 (1.4 g, 5.3 mmol) in $CH_2Cl_2$; The mixture was stirred at −78° C. under nitrogen for three hours and then at room temperature overnight. After the mixture was cooled to −78° C., methanol (50 mL) was added dropwise and the solvent was removed by reduced pressure. The residue was dissolved in methanol (100 mL) and the solution was refluxed under nitrogen for 2 hours. After removal of solvent, chromatography ($SiO_2$, 10% MeOH in $CH_2Cl_2$) of the residue yielded the title compound as a dark brown solid (1.65 g, 4.94 mmol, 93% yield). MS (ESI) m/z 254 ($MH^+$);

$^1$H NMR (DMSO-$d_6$) δ 9.50 (br, s, 2H), 9.28 (s, 1H), 8.54 (s, 1H), 7.32 (d, 1H, J=8.3 Hz), 7.23 (t, 1H, J=8.3 Hz), 7.12 (d, 1H, J=8.5 Hz), 6.70 (d, 1 H, J=9.3 Hz), 6.54 (d, 1H, J=6.7 Hz), 4.37 (s, 2H), 4.30–4.23 (m, 2H), 3.97 (m, 1H), 3.45–3.31 (m, 2H); $^{13}$C NMR (DMSO-$d_6$) δ 143.8, 142.0, 136.9, 132.1, 127.6, 127.0, 126.6, 124.1, 123.7, 114.0, 112.7, 48.6, 44.0, 32.9, and 28.5. Anal. Calcd. for $C_{16}H_{15}NO_2$.1.28HBr.0.59$H_2O$: C, 52.34; H, 4.79; N, 3.82. Found: C, 52.29; H, 4.92, N, 4.14.

EXAMPLE 12

12H-Benzo[d,e][1,3]benzodioxol[4,5-h]isoquinoline

A sample of (±)-8,9-methylenedioxy-2,3,7,11b-tetrahydro-1H-napth[1,2,3-de]isoquinoline (651 mg) was dissolved into 250 mL of reagent grade xylenes. To this solution was added 40 mg of 5% Pd on charcoal catalyst and the suspension was warmed to reflux under nitrogen atmosphere. A small aliquot was removed after 24 hr and was analyzed by LC/MC to show complete oxidation. The catalyst was removed by filtration through a short bed of silica gel (Type-H) and the orange color filtrate was concentrated under reduced pressure to give 640 mg of dark orange crystals. The NMR of this sample of the title compound was indistinguishable from a sample prepared in Example 7.

EXAMPLE 13

(±)-N-Methyl-8,9-Dihydrox-2,3,7,11b-tetrahydro-1H-napth[1,2,3-de]isoquinoline

Step A. N-Methyl-12H-benzo[d,e][1,3]benzadioxol[4,5-h]isoquinoline

To a solution of 12H-benzo[d,e][1,3]benzodioxol[4,5-h]-isoquinoline (0.38 mmol) in warm dichloroethane (4 mL), methyl iodide (12.8 mmol) was added and after a few minutes a yellow suspension was observed. The reaction was warmed to 40° C. with stirring for 20 minutes. After all the starting material was gone, nitrogen was blown into the system to remove both the solvent and excess MeI and then dried further under high vacuum. The resulting yellow residue was resuspended in THF and then sodium triacetoxyborohydride (0.4 g) and sodium cyanoborohydride (0.12 g) were added. After a few minutes the suspension turns orange and stirring was continued for 20 minutes. Saturated ammonium chloride and hydrochloric acid (2N) were added to the suspension to form two layers. Then sodium cyanoborohydride (0.12 g) was added and stirred for 30 minutes. The layers were separated and the organic layer was evaporated and dried under vacuo. Partial isolation and purification of product was achieved by recrystallization to give the title compound (0.047 g) and the mother liquor was purified by column filtration to afford more product (0.04 g, 82% yield):

$^1$H NMR (DMSO-$d_6$) δ 7.39 (d, 1H, J=7.35 Hz), 7.28 (t, 1H, J=7.47 Hz), 7.13 (d, 1H, J=7.29 Hz), 6.86 (d, 1H, J=8.04 Hz), 6.72 (d, 1H, J=7.95 Hz), 6.09 (s, 1 Hz), 6.02 (s, 1H), 4.60–4.25 (m, 3H), 4.20–4.03 (m, 2H), 3.75–3.68 (m, 1H), 3.60–3.40 (m, 1H), 3.02 (s, 3H); LCMS Calcd. for $C_{18}H_{17}NO_2$ ($M^+$): 279.13. Found: ($MH^+$) 280.13.

Step B. (±)-N-Methyl-8,9-Dihydroxy-2,3,7,11b-tetrahydro-1H-napth[1,2,3-de]isoquinoline To a solution of the compound of Step A (0.16 mmol) in dichloromethane (4 mL) cooled to −78° C., boron tribromide (1M in dichloromethane, 0.77 mmol) was added. The reaction solution was stirred at −78° C. for two hours and warned to room temperature overnight. The solution was cooled to −78° C. and dry methanol was added to quenched the reaction. After stirring for to minutes, the solvent was removed and dry methanol was added. The process was repeated three times. Purification was performed by recrystallization with MeOH/$CH_2CH_2$ to obtain the title compound (0.035 g):

$^1$H NMR (MeOD-$d_3$) δ 7.37 (d, 1H, J=7.26 Hz), 7.29 (t, 1H, J=7.35 Hz), 7.11 (d, 1H, J=7.32 Hz), 6.72 (d, 1H, J=8.19 Hz), 6.59 (d, 1H, J=8.49), 4.7–4.39 (m, 3H), 4.20–4.05 (m, 1H) 3.70–3.40 (m, 2H), 3.20 (s, 3H); LCMS Calcd. for $C_{17}H_{17}NO_2$ ($M^+$): 267.13. Found: ($MH^+$) 268.16.

What is claimed is:

1. A process for preparing a compound of the formula

IX

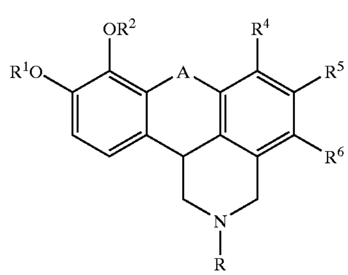

wherein $R^1$ and $R^2$ each are hydrogen; A is $CH_2$, CHOH or C═O; R is hydrogen or $C_{1-4}$alkyl; and $R^4$, $R^5$ and $R^6$ each are independently hydrogen, $C_{1-4}$alkyl, $C_{1-4}$alkoxy, hydroxy or halogen, comprising the steps of (a) reducing a compound of the formula

VII

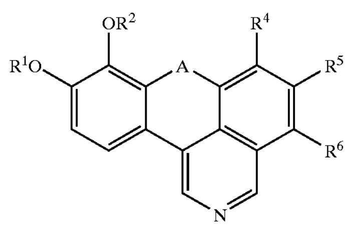

wherein $R^1$ and $R^2$ each are a hydroxy-protecting group; or $R^1$ and $R^2$ may be joined together to form —$(CH_2)_n$— in which n is 1 to 3 and $R^4$, $R^5$ and $R^6$ and A are as defined above; with a reducing agent and (b) deprotecting the resulting reduced product to produce the compound of Formula IX wherein $R^1$ and $R^2$ are hydrogen and (c) optionally, alkylating the product of step (a) or (b) to produce a compound of Formula IX wherein R is $C_{1-4}$alkyl.

2. The process of claim 1 wherein A is $CH_2$.

3. The process of claim 2 wherein $R^1$ and $R^2$ are joined together to form —$(CH_2)_n$— in which n is 1.

4. The process of claim 3 wherein and $R^4$, $R^5$ and $R^6$ are hydrogen.

5. The process of claim 1 wherein said reducing agent is sodium cyanoborohydride.

6. The process of claim 1 wherein said deprotecting agent is boron tribromide.

7. A compound of the formula

IX

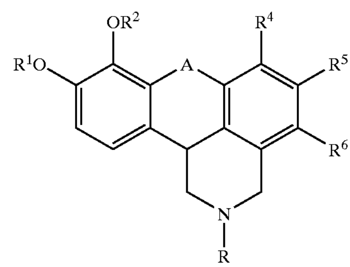

wherein $R^1$ and $R^2$ each are hydrogen or a hydroxy-protecting group; or $R^1$ and $R_2$ may be joined together to form —$(CH_2)_n$—, n is 1 to 3;

A is $CHOR^1$ or C═O;

R is hydrogen or $C_{1-4}$alkyl; and $R^4$, $R^5$ and $R^6$ each are independently hydrogen, $C_{1-4}$alkyl, $C_{1-4}$alkoxy, hydroxy or halogen.

8. The compound of claim 7 wherein $R^1$ and $R^2$ are hydrogen and A is $CHOR^1$ in which $R^1$ is hydrogen.

9. The compound of claim 7 wherein $R^1$ and $R^2$ are hydrogen and A is C═O.

10. The compound of claim 8 wherein $R^4$, $R^5$ and $R^6$ are hydrogen.

11. The compound of claim 10 wherein R is hydrogen.

12. A pharmaceutical composition for the treatment of dopamine-related disorders comprising a therapeutically effective amount of a compound as defined in claim 7 in association with a pharmaceutically acceptable carrier or diluent.

13. A method for the treatment of dopamine-related disorders in a mammal in need thereof, which comprises administering to said mammal a therapeutically effective amount of a compound as defined in claim 7.

* * * * *